(12) United States Patent
Yamakawa (10) Patent No.: US 7,316,198 B2
(45) Date of Patent: Jan. 8, 2008

(54) HUMIDITY INDICATOR

(76) Inventor: Yoichi Yamakawa, 1-17-1-208, Gakuennishi-machi, Kodaira-shi, Tokyo 187-0045 (JP)

( * ) Notice: Subject to any disclaimer, the term of this patent is extended or adjusted under 35 U.S.C. 154(b) by 0 days.

(21) Appl. No.: 10/581,278

(22) PCT Filed: Nov. 26, 2004

(86) PCT No.: PCT/JP2004/017979

§ 371 (c)(1),
(2), (4) Date: Jun. 1, 2006

(87) PCT Pub. No.: WO2005/054842

PCT Pub. Date: Jun. 16, 2005

(65) Prior Publication Data

US 2007/0113775 A1    May 24, 2007

(30) Foreign Application Priority Data

Dec. 2, 2003    (JP)    ............................. 2003-436211

(51) Int. Cl.
*G01D 21/00* (2006.01)
*G01N 31/22* (2006.01)

(52) U.S. Cl. ............................. 116/206; 116/DIG. 41; 422/58

(58) Field of Classification Search ................ 116/206, 116/DIG. 41; 422/56, 58, 61; 436/164, 436/168, 169
See application file for complete search history.

(56) References Cited

U.S. PATENT DOCUMENTS

| | | | | |
|---|---|---|---|---|
| 2,716,338 A | * | 8/1955 | Blinn | ............................. 73/73 |
| 3,198,163 A | * | 8/1965 | Williams | .................... 116/206 |
| 5,224,373 A | * | 7/1993 | Williams et al. | ............ 73/29.02 |
| 5,310,525 A | * | 5/1994 | Churchouse et al. | .......... 422/56 |
| 5,520,041 A | * | 5/1996 | Haswell | ..................... 73/29.04 |
| 5,875,892 A | * | 3/1999 | Martin et al. | ............. 206/459.1 |
| 6,603,318 B2 | * | 8/2003 | Hansen et al. | .............. 324/689 |

(Continued)

FOREIGN PATENT DOCUMENTS

JP    63-48455 A    3/1988

(Continued)

*Primary Examiner*—Diego Gutierrez
*Assistant Examiner*—Amy R. Cohen
(74) *Attorney, Agent, or Firm*—Arent Fox LLP (57) ABSTRACT

A humidity indicator includes a first film (F1) covering a surface of a humidity-determining plate (B), and a second film (F2) covering a back of the humidity-determining plate (B). A flat air layer (Au) is formed at least between the first film (F1) and the surface of the humidity-determining plate (B), so that the entire surfaces of humidity-determining faces (M1 to M4), to which cobalt chloride (CO) is exposed, face to the air layer (Au), and a plurality of small holes (H) are formed at distances from one another in the first film (F1) to permit the direct communication of the air layer (Au) with the atmosphere. Therefore, even if an operator picks, with his or her hand, a humidity indicator for determining humidity by the discoloration of cobalt chloride, the cobalt chloride on a humidity-determining face is prevented effectively from adhering to the operator's hand and thus, entering into his or her body. In addition, even if fine dust is generated from a base paper sheet of the humidity indicator, it is hard for the dust to be diffused to the surroundings, thereby effectively preventing the influence of the dust to electronic parts.

10 Claims, 4 Drawing Sheets

U.S. PATENT DOCUMENTS

| | | | |
|---|---|---|---|
| 6,698,378 B1 * | 3/2004 | Dick et al. | 116/206 |
| 6,827,218 B1 * | 12/2004 | Dick et al. | 206/720 |
| 6,877,457 B1 * | 4/2005 | Dick et al. | 116/206 |
| 7,185,601 B2 * | 3/2007 | Carpenter et al. | 116/206 |

FOREIGN PATENT DOCUMENTS

| | | |
|---|---|---|
| JP | 64-69951 A | 3/1989 |
| JP | 6-43155 A | 2/1994 |
| JP | 2000-107551 A | 4/2000 |
| KR | 20-0280827 | 6/2002 |

* cited by examiner

FIG.1

HUMIDITY INDICATOR

CROSS-REFERENCE TO RELATED APPLICATION

This application is a National Stage entry of International Application Number PCT/JP2004/017979, filed Nov. 26, 2004. The disclosure of the prior application is hereby incorporated herein in its entirety by reference.

TECHNICAL FIELD

The present invention relates to a humidity indicator which is designed so that the discoloration of cobalt chloride in accordance with a change in humidity can be utilized for the determination of humidity.

BACKGROUND ART

There is a conventionally known a humidity indicator of the above-described type, having a structure including a humidity-determining face which is provided on a surface of a humidity-determining plate, for example, comprising cobalt chloride held in a base paper sheet, so that the cobalt chloride is exposed to the humidity-determining face, whereby the determination of humidity around the base paper sheet can be visually conducted by the discoloration (from blue to pink) of the cobalt chloride on the humidity-determining face.

Such a humidity indicator is used in a state in which it has been sealedly contained in a transparent air-tight packaging bag along with a variety of industrial products adversely affected by moisture (e.g., electronic parts such as circuit boards which may be cracked by the absorption of moisture by an epoxy resin) and a drying agent in the transportation of the industrial products. In the transportation of the products in such used state, whether or not the humidity in the packaging bag exceeds a defined limit can be visually determined by the color of the humidity-determining face of the humidity indicator. Therefore, whether the inside of the packaging bag with the drying agent contained therein is kept in an appropriate humidity state (a dried state) can be checked easily and hence, such humidity indicator is conventionally widely used in an electronic industry and the like.

In the conventional humidity indicator, both of the surface and back of the humidity-determining plate (hence, even the humidity-determining face to which the cobalt chloride is exposed) are placed in states exposed to the outside, and an operator picks the humidity-determining plate directly with his or her hand and withdraws and places it out of and into a dry pack.

DISCLOSURE OF THE INVENTION

Problems to be Solved by the Invention

To open the packaging bag and remove a product or products from the packaging bag, it is a conventional practice that the operator picks the humidity indicator with his or her hand to take it out of the pack, and checks the colors of the humidity-determining face, as described above. For this reason, there is a possibility that the cobalt chloride on the humidity-determining face might adhere to the operator's hand and enter into the operator's body. It is known that the cobalt chloride is cancerogenic, and hence, it is desirable to improve an operating environment having a possibility that such cobalt chloride, even if in a very small amount, might adhere to the operator's hand and enter into the operator's body.

In addition, in the conventional humidity indicator, the humidity-determining face is in the state exposed to the outside. For this reason, when the humidity indicator has been taken in the atmosphere out of a sealed storage container or a packaging bag with a drying agent contained therein as described above, of which interior is maintained in a low-humidity state, the cobalt chloride on the humidity-determining face is discolored relatively quickly due to the direct contact with air in a room, resulting in the arising of the following problem: Upon opening of the packaging bag and removal of the humidity indicator out of the packaging bag, when the humidity-determining face is discolored in a relatively short time, the operator may overlook the color before discoloration to provide an erroneous determination. In a case where an unused humidity indicator is taken out of a sealed storage container and transferred into the packaging bag, when the discoloration occurs before the transferring due to the slow working or the like, the user may erroneously recognize the humidity indicator as a defective indicator, causing various problems.

The base paper sheet of the humidity indicator is conventionally formed of a filter paper or another paper, but in the case of such paper, particularly, the filer paper, fine dust (paper scraps and fiber) is liable to be generated from an outer surface or a cut face of such paper. When the dust adheres to an electronic part, there is a possibility that the performance of the electronic part may be influenced. Therefore, it is desirable to prevent the dust generated from the base paper sheet from being diffused to the outside.

Further, there is a possibility that when another part or a packaging material in a charged state is brought near to the electronic part, the performance of the electronic part may be influenced and moreover, dust is liable to adhere to the part or the like in the charged state by a static electricity. Therefore, it is desirable that the humidity indicator itself is hard to be charged with electricity as much as possible in view of avoiding the influence of electrostatic charge and the influence of the dust.

The present invention has been accomplished with the above-described circumstances in view, and it is an object of the present invention to solve the above-described conventional problems in a simple structure.

Means for Solution of the Problems

To achieve the above object, according to a first feature of the present invention, there is provided a humidity indicator, comprising at least one humidity-determining face which is provided on a surface of a humidity-determining plate comprising cobalt chloride held in a base paper sheet, so that the cobalt chloride is exposed to the humidity-determining face, whereby humidity is determined by the discoloration of the cobalt chloride on the humidity-determining face, characterized in that the humidity indicator further includes a first film covering the surface of the humidity-determining plate, and a second film covering the back of the humidity-determining plate; a flat air layer is formed at least between the first film and the surface of the humidity-determining plate, so that the entire surface of the humidity-determining face faces to the air layer; and a plurality of small holes are formed at distances from one another in the first film to permit the direct communication of the air layer with the atmosphere.

According to a second feature of the present invention, in addition to the first feature, the first and second films are formed to protrude from an outer peripheral edge of the humidity-determining plate and bonded at outer peripheral edge portions thereof directly to each other.

According to a third feature of the present invention, in addition to the first or second feature, a plurality of the humidity-determining faces are arranged at distances on the surface of the humidity-determining plate in correspondence to a plurality of different humidity levels, respectively, and the air layer is formed commonly to the plurality of humidity-determining faces.

According to a fourth feature of the present invention, in addition to any of the first to third features, the base paper sheet is a filter paper having a hygroscopicity; a flat second air layer is formed between the second film and the back of the humidity-determining plate, so that at least a region or regions of the back corresponding to the humidity-determining face or faces face to the second air layer; and a plurality of small holes are formed at distances from one another in the second film to permit the direct communication of the second air layer with the atmosphere.

According to a fifth feature of the present invention, in addition to any of the first to fourth features, each of the films has been subjected to an antistatic treatment.

EFFECT OF THE INVENTION

As described above, with each of the first to fifth features of the present invention, the surface and back of the humidity-determining plate are covered with the first and second films. Therefore, even if an operator directly picks the humidity indicator with his or her hand, the cobalt chloride on the humidity-determining face can be prevented effectively from adhering to the hand and thus, entering into the operator's body, and the operator can handle the humidity indicator without anxiety. In addition, the humidity indicator is of such a structure that even if fine dust (such as paper scraps and fiber) is generated from the base paper sheet of the humidity indicator, it is blocked off each of the films and hard to be diffused to the outside. Therefore, even if the humidity indicator is sealedly accommodated along with electronic parts and the like adversely affected by dust, the influence of dust to the electric parts can be prevented effectively.

Further, the flat air layer is formed between the first film and the surface of the humidity-determining plate, so that the entire humidity-determining face faces to the air layer, and the plurality of small holes are formed at the distances from one another in the first film to permit the direct communication of the air layer with the atmosphere. Therefore, when the humidity indicator has been taken in the atmosphere out of a sealed storage container or the like whose inside is kept in a low-humidity state, a time lag is ensured which is moderate for the humidity in the air layer to be changed in accordance with the humidity in the atmosphere. Therefore, a time lapsed to a time point of discoloration of the humidity-determining face (a time required for the discoloration) can be set moderately. This is effective for preventing the erroneous determination or the arising of a trouble, which is likely caused when the time is relatively short. Moreover, the length of the time lag (and hence, the time required for the discoloration) can be regulated easily in accordance with the purpose of use, the working environment and the like by properly setting the density of dispersion, the inside diameter and the like of the plurality of small holes. In addition, if the humidity-determining face is provided to face directly to the small holes, then there is a problem that only the cobalt chloride at a portion corresponding to each of the small holes is partially discolored, and as a result, the appearance is degraded, and moreover, the determining operation is hard to conduct. However, according to the present invention, the air layer is interposed between the small holes and the humidity-determining faces and hence, not only the portions corresponding to the small holes but also the entire surfaces of the humidity-determining faces can be discolored uniformly, and thus, such problem can be eliminated.

Particularly, with the second feature of the present invention, the first and second films are formed to protrude from the outer peripheral edge of the humidity-determining plate, and bonded at their outer peripheral edges directly to each other. Therefore, the outer peripheral edge of the base paper sheet can be covered completely with the first and second films and hence, it is possible to reliably prevent the generation of dust from a cut face of the outer periphery of the base paper sheet. In addition, because the films are bonded directly to each other, it is possible to carry out the bonding operation relatively easily and reliably, leading to the simplification of the bonding step.

Particularly, with the third feature of the present invention, a plurality of the humidity-determining faces are arranged at the distances on the surface of the humidity-determining plate in correspondence to a plurality of different humidity levels, and the air layer is formed commonly to the plurality of humidity-determining faces. Therefore, the step for forming the air layer is simplified, as compared with a case where air layers are formed for every humidity-determining faces.

Particularly, with the fourth feature of the present invention, the base paper sheet of the humidity-determining plate is the filter paper having the hygroscopicity; the flat second air layer is formed between the second film and the back of the humidity-determining plate, so that at least the region or regions of the back corresponding to the humidity-determining face or faces face to the second air layer; and the plurality of small holes are formed at distances from one another in the second film to permit the direct communication of the second air layer with the atmosphere. Therefore, when the humidity indicator has been taken in the atmosphere out of a sealed storage container or the like, the humidity in the atmosphere is transmitted from the back side of the base paper sheet through the inside of the base paper sheet even to the surface-side air layer. Accordingly, it is possible to more enhance the sensitivity of portions of the humidity-determining faces on the side of the surface to the change in humidity.

Particularly, with the fifth feature of the present invention, the films have been subjected to the antistatic treatment and hence, the humidity-determining plate itself is hard to charge with electricity and moreover, it is hard for dust to adhere to the films by static electricity. Thus, even if the humidity indicator is sealedly accommodated along with electronic parts, it is possible to avoid the influence of charging to the electronic parts and the influence of dust as much as possible.

EXPLANATION OF REFERENCE NUMERALS AND CHARACTERS

Ad . . . back-side air layer (second air layer)
Au . . . surface-side air layer
B . . . base paper sheet
Co . . . cobalt chloride
F1 . . . first film
F2 . . . second film
H, H' . . . small hole
I . . . humidity indicator
M1 to M4 . . . first to fourth humidity-determining faces
P . . . humidity-determining plate

BEST MODE FOR CARRYING OUT THE INVENTION

The mode for carrying out the present invention will now be described in detail by way of an embodiment of the present invention with reference to the accompanying drawings.

Embodiment 1

In the accompanying drawings, FIGS. 1 to 4 show one embodiment of the present invention.

A humidity indicator I used for visual determination of humidity is formed of a humidity-determining plate P of a flat plate-shape, and a cover member C for covering the humidity-determining plate P.

Figure 1:
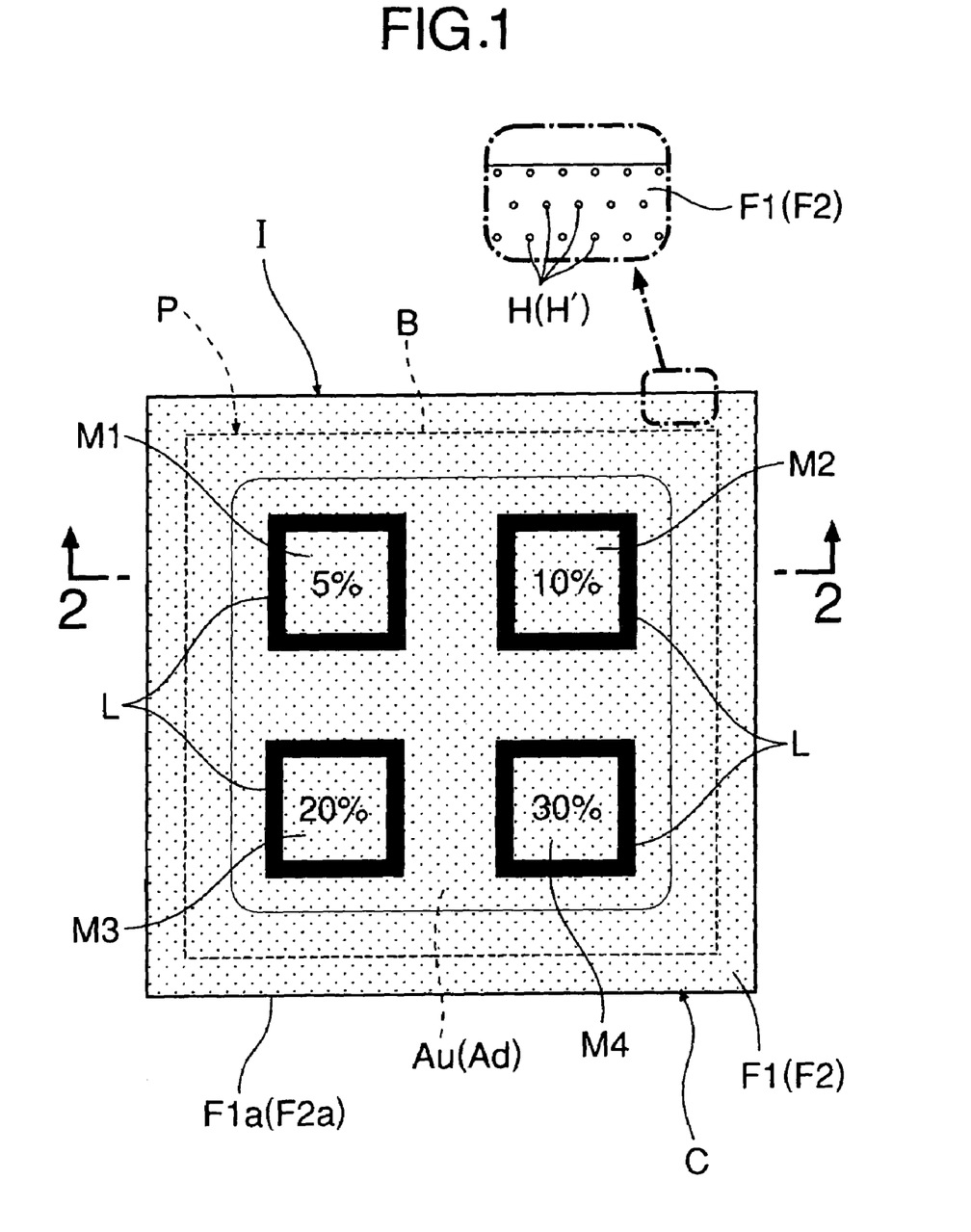
FIG. 1 is a plan view of the whole of a humidity indicator with an enlarged view of a portion of the humidity indicator according to one embodiment of the present invention. (Embodiment 1)

The humidity-determining plate P includes a base paper sheet B made of a filter paper having a hygroscopicity, and cobalt chloride Co held in the base paper sheet B. The base paper sheet B is formed into a card-shape (a square shape in the illustrated embodiment) and has a plurality of humidity-determining faces M1 to M4 provided on its surface, to which the cobalt chloride Co is exposed, so that humidity can be determined achieved by the degree of discoloration of the cobalt chloride Co on the humidity-determining faces M1 to M4.

In the illustrated embodiment, exposed to the first humidity-determining face M1 is the cobalt chloride Co which has been previously adjusted so that it remains blue when humidity of an atmosphere containing the humidity indicator I placed therein is equal to or lower than 5%, but it is discolored to pink when the humidity is increased in excess of 5%. Exposed to the second humidity-determining face M2 is the cobalt chloride Co which has been previously adjusted so that it remains blue when the humidity of the atmosphere is equal to or lower than 10%, but it is discolored to pink when the humidity is increased in excess of 10%. Further, exposed to the third humidity-determining face M3 is the cobalt chloride Co which has been previously adjusted so that it remains blue when the humidity of the atmosphere is equal to or lower than 20%, but it is discolored to pink when the humidity is increased in excess of 20%. Yet further, exposed to the fourth humidity-determining face M4 is the cobalt chloride Co which has been previously adjusted so that it remains blue when the humidity of the atmosphere is equal to or lower than 30%, but it is discolored to pink when the humidity is increased in excess of 30%.

The plurality of humidity-determining faces M1 to M4 are arranged two by two longitudinally and transversely, respectively, but the arrangement of them may be selected as desired. For example, they may be arranged either transversely in one row or longitudinally in one row.

In the illustrated embodiment, solutions of cobalt chloride having concentrations regulated to be able to exhibit discoloration characteristics corresponding to the humidity-determining faces M1 to M4 are dropped from above onto, permeated into and held in the base paper sheet B. Thus, portions of the surface of the base paper sheet B corresponding to positions of dropping of the cobalt chloride solutions are the humidity-determining faces M1 to M4. Black bold rines L have been printed in a proper shape (a quadrilateral shape in the illustrated embodiment) on the surface of the base paper sheet B for clearly indicating borders between the humidity-determining faces M1 to M4, while respectably hiding the permeation of the solutions into peripheral edges of the portions, onto which the solutions have been dropped. Further, indications (5%, 10%, 20% and 30%) of limit humidity values capable of being checked by the humidity-determining faces M1 to M4 have been printed on or in the vicinity of the humidity-determining faces M1 to M4. The structure of the humidity-determining plate P described above is conventionally well-known.

Figure 2:
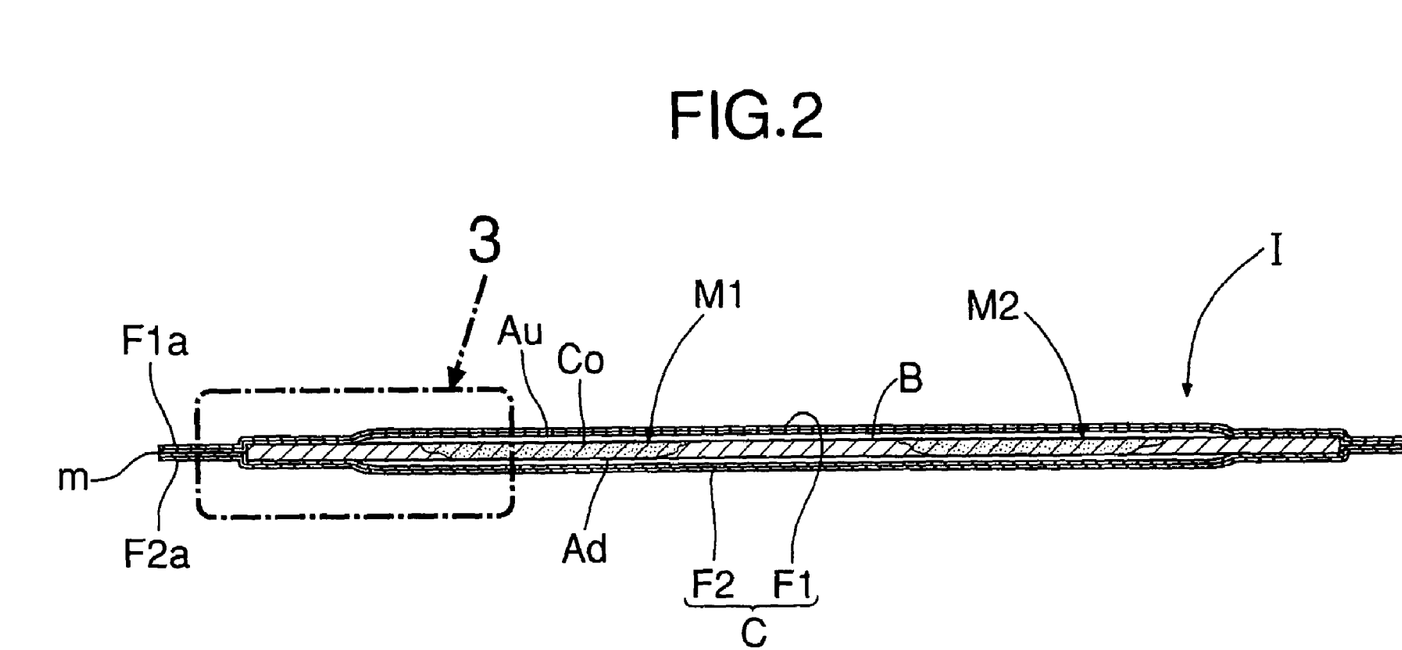
FIG. 2 is an enlarged vertical sectional view taken along a line 2-2 in FIG. 1. (Embodiment 1)
Figure 3:
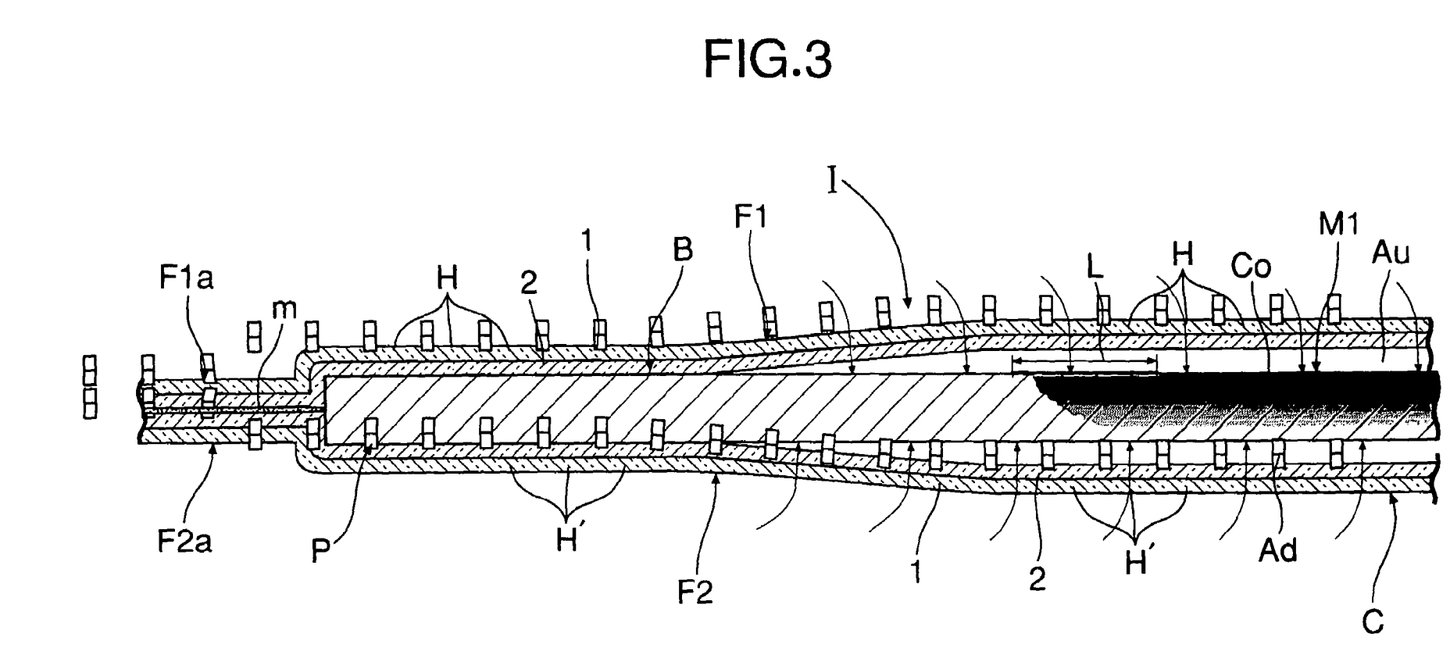
FIG. 3 is an enlarged sectional view taken in the direction of an arrow 3 in FIG. 2. (Embodiment 1)

On the other hand, the cover member C is comprised of a first film F1 covering the surface of the humidity-determining plate P, and a second film F2 covering the back of the humidity-determining plate P. The first and second films F1 and F2 are formed to protrude from an outer peripheral edge of the humidity-determining plate P and bonded at m at their peripheral edges F1a and F2a directly to each other, so that the entire resulting film assembly is formed into a flat quadrilateral bag-shape.

Each of the films F1 and F2 is formed of a transparent film made of a synthetic resin, and in the illustrated embodiment, it is of a two-layer structure comprising an outer resinous layer 1 formed of a stout synthetic resin material (e.g., polyester, nylon or the like) having a relatively high melting point and a high strength, and an inner resinous layer 2 formed of a synthetic resin material (e.g., polyethylene, EVA or the like) having a relatively low melting point, these layers being integrally bonded to each other. The direct bonding m of the outer peripheral edges F1a and F2a of the films F1 and F2 is achieved by bringing the inner resinous layers 2, 2 of the films F1 and F2 into direct contact with each other and subjecting them to a thermo-compression bonding treatment. In this case, the outer resinous layers 1 of the films F1 and F2 having the relatively high melting point are brought into direct contact with heated rolls or the like used for the thermo-compression bonding treatment and hence, the resin does not stick strongly to the heated rolls or the like, leading to a good processability.

The outer resinous layer 1 is subjected to an antistatic treatment. A process for the antistatic treatment is, for example, to incorporate an antistatic agent into the outer resinous layer 1, or to subject a surface of the outer resinous layer 1 (a surface opposite from the inner resinous layer 2) to an antistatic processing.

A flat surface-side air layer Au is formed between the first film F1 and the surface of the humidity-determining plate P, so that the entire humidity-determining faces M1 to M4 face to the surface-side air layer Au. Namely, the first film F1 is bonded in the thermo-compression manner to the surface of the humidity-determining plate P, excluding a region corresponding to the surface-side air layer Au. A small clearance created between the first film F1 and the humidity-determining plate P in the region where the thermo-compression bonding is not carried out, forms the surface-side air layer Au. In the illustrated embodiment, the surface-side air layer Au is formed into a planar shape including all of the humidity-determining faces M1 to M4 and as a common air layer to which all of the humidity-determining faces M1 to M4 face.

In addition, a flat back-side air layer Ad is formed between the second film F2 and the back of the humidity-determining plate P, so that at least regions of the back corresponding to the humidity-determining faces M1 to M4 (the entire back in the illustrated embodiment) face to the flat back-side air layer Ad. A method for forming the back-side air layer Ad is similar to the method for forming the surface-side air layer Au.

A large number of small holes H are formed at distances from one another in the first film F1 to permit the direct communication of the surface-side air layer Au with the atmosphere, and a large number of small holes H' are also formed at distances from one another in the second film F2 to permit the direct communication of the back-side air layer Ad with the atmosphere. In the illustrated embodiment, for convenience of the processing, the small holes H and H' are made in not only portions corresponding to the air layers Au and Ad but also the entire surfaces of the films F1 and F2.

The inside diameter of the small holes H is set at a value (0.8 mm in the illustrated embodiment) such that when an operator holds the humidity indicator I with his or her hand, his or her fingers contacting with each of the films F1 and F2 do not touch the cobalt chloride Co on the humidity-determining faces M1 to M4 directly. Moreover, the density of dispersion and the inside diameter of the small holes H and H' are set so that even when the humidity indicator I has been taken in the atmosphere out of a packaging bag, a sealed storage container or the like in a low-humidity state, a time lag moderate for the humidity of the air layers Au and Ad to change in accordance with the humidity of the atmosphere is ensured, whereby the cobalt chloride Co on the humidity-determining faces M1 to M4 can be prevented from being discolored in a relatively short time, which is effective for preventing the erroneous determination or a trouble due to the discoloration.

In the present embodiment, for example, 560 small holes H, H' having an inside diameter of 0.8 mm are formed at equal distances in each of the square films F1 and F2 of 40 mm square, and the density of dispersion is 35/cm². In this case, when a time taken for the cobalt chloride Co to be discolored completely from blue to pink is measured, the time is approximately 5 to 7 minutes on the first humidity-determining face (the limit humidity of 5%), approximately 15 to 20 minutes on the second humidity-determining face (the limit humidity of 10%), approximately 30 to 35 minutes on the third humidity-determining face (the limit humidity of 20%) and approximately 45 to 50 minutes on the fourth humidity-determining face (the limit humidity of 30%), depending on the humidity of a surrounding atmosphere at that time. On the other hand, when the same humidity-determining plate P is used in an exposed state without being covered with the cover member C, a time taken for the discoloration is approximately 4 to 5 minutes on the first humidity-determining face (the limit humidity of 5%), approximately 10 to 15 minutes on the second humidity-determining face (the limit humidity of 10%), approximately 20 to 25 minutes on the third humidity-determining face (the limit humidity of 20%) and approximately 35 to 40 minutes on the fourth humidity-determining face (the limit humidity of 30%). It can be seen that the time taken for the discoloration in the present embodiment is moderately longer than that in the comparative example.

In FIG. 3, the air layers Au and Ad and the films F1 and F2 are shown with their thicknesses somewhat magnified more than actual scales for ease of understanding.

Figure 4:
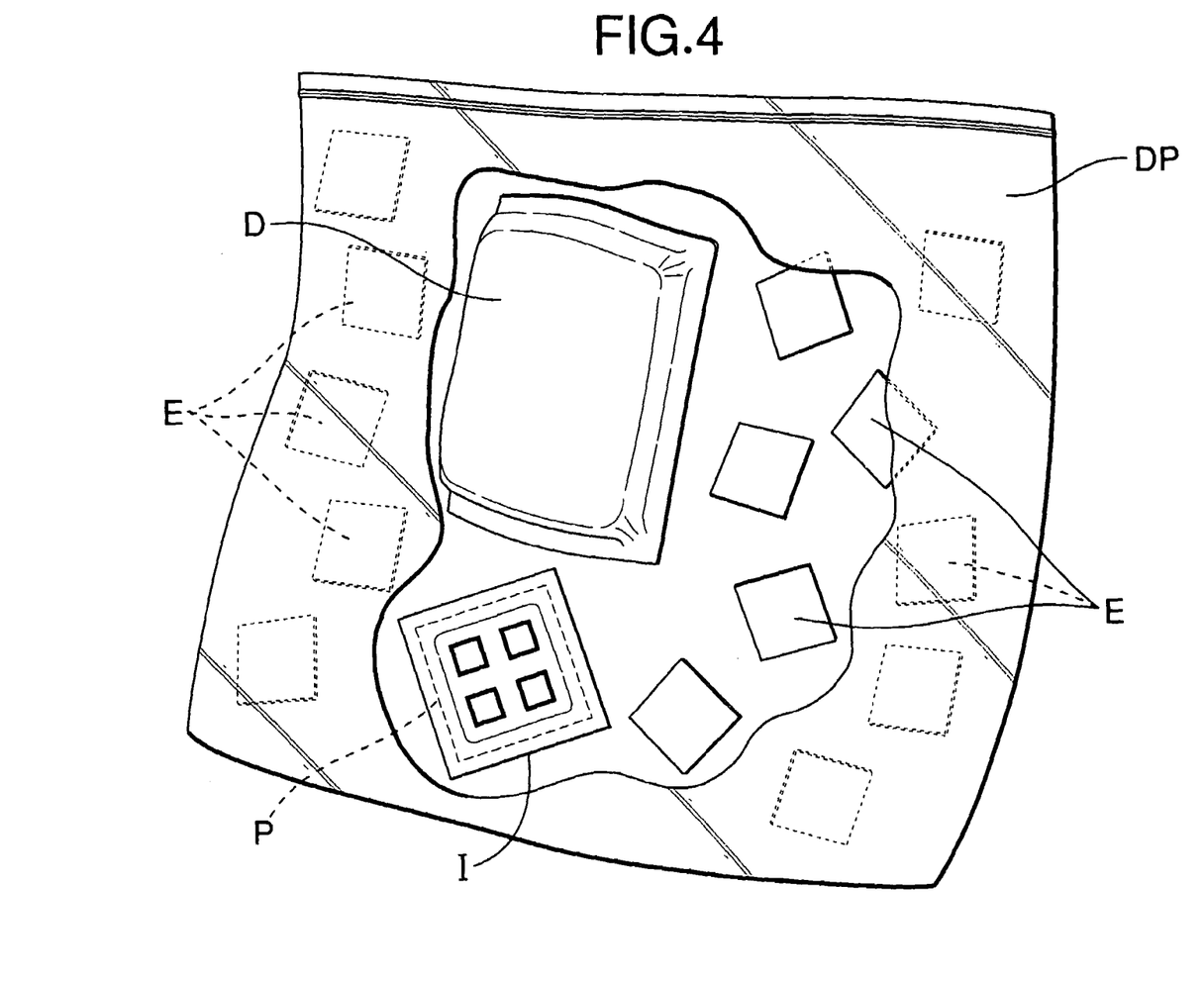
FIG. 4 is a perspective view showing the humidity indicator in a state in which it has been sealedly incorporated in a packaging bag along with electronic parts and a drying agent. (Embodiment 1)

The operation of the above-described embodiment will be described below. The humidity indicator I of the present embodiment is used as remaining sealedly contained along with electronic parts E and a drying agent D in a transparent air-tight packaging bag DP, as illustrated in FIG. 4 in the transportation of the electronic parts such as circuit boards adversely affected by moisture, and the electronic parts E are transported as remaining contained in the packaging bag DP. A container provided with a lid for sealing may be used in place of such packaging bag.

During the transportation, whether or not the humidity in the packaging bag DP does not exceed a defined limit can be visually determined by the colors of the humidity-determining faces M1 to M4 of the humidity indicator I (based on whether or not the humidity-determining faces M1 to M4 have been discolored). Therefore, it is possible to easily check whether or not the inside of the packaging bag DP with the drying agent D contained therein is kept in a proper humidity state (a dried state) during the transportation.

When the packaging bag DP is opened to remove the electronic parts E, the operator picks the humidity indicator I with his or her hand, takes it out of the packaging bag and checks the colors of the humidity-determining faces M1 to M4. The surface and back of the humidity-determining plate P are covered with the first and second films F1 and F2 in the humidity indicator I of the present embodiment, and hence, even if the operator has picked the humidity indicator I directly with his or her hand, it is possible to effectively prevent the cobalt chloride Co on the humidity-determining faces M1 to M4 from adhering to the operator's hand and thus, from entering into the operator's body. Thus, the operator can handle the humidity indicator I without anxiety. In addition, the humidity indicator I is of a structure such that even if fine dust (such as paper scraps and fiber) is generated from the base paper sheet B of the humidity-determining plate P, it is blocked off by the films F1 and F2 and hard to be diffused to the outside. Therefore, even if the humidity indicator I is sealedly contained in the packaging bag DP along with the electronic parts E disliking a dust, an adverse influence of a dust to the electronic parts E can be prevented effectively.

Moreover, in the illustrated embodiment, the films F1 and F2 (particularly, the outer resinous layer 1) have been subjected to the antistatic treatment, and hence, the covered humidity-determining plate P itself is hard to be charged with electricity, and moreover, it is hard for a dust to adhere to the films F1 and F1 by static electricity. Therefore, even if the humidity indicator I is sealedly contained within the packaging bag DP along with the electronic parts E, it is possible to avoid the influence of charging of the electronic parts E with electricity and the influence of the dust as much as possible.

Particularly, the flat surface-side air layer Au is formed between the first film F1 and the surface of the humidity-determining plate P, so that the first to fourth humidity-determining faces M1 to M4 face to the flat surface-side air layer Au, and the large number of small holes H are formed at the distances from one another in the first film F1 to permit the direct communication of the air layer Au with the atmosphere. Therefore, when the humidity indicator I has been taken in the atmosphere out of the packaging bag DP or the like kept in the low-humidity state, the time lag is ensured which is moderate for the humidity in the air layer to be changed in accordance with the humidity in the atmosphere and hence, the cobalt chloride Co on each of the humidity-determining faces M1 to M4 can be prevented from being discolored in a relatively short time, i.e., the time lapsed to a time point of discoloration of each of the humidity-determining faces M1 to M4 (the time required for the discoloration) can be set moderately neither too much nor too little. This is effective for preventing the erroneous determination and the arising of a trouble due to the relatively short time. Moreover, the length of the time lag (and hence, the time required for the discoloration) can be regulated easily in accordance with the purpose of use, the working environment and the like by properly setting the density of dispersion, the inside diameter and the like of the small holes H.

If the humidity-determining faces M1 to M4 are provided to face directly (i.e., without through the surface-side air layer Au) to the small holes H, then there is a problem that only the cobalt chloride Co at a portion of each of the humidity-determining faces M1 to M4 corresponding to each of the small holes H is partially discolored, and as a result, the appearance is degraded, and moreover, the determining operation is hard to conduct. However, the interposition of the surface-side air layer Au between the small holes H and the humidity-determining faces M1 to M4 as in the present embodiment ensures that not only the portions corresponding to the small holes but also the entire surfaces of the humidity-determining faces M1 to M4 can be discolored uniformly, and thus, such problem can be eliminated.

Particularly, the first and second films F1 and F2 are formed to protrude from the outer peripheral edge of the humidity-determining plate P and bonded at m at their outer peripheral edges F1a and F2a directly to each other. Therefore, the outer peripheral edge of the base paper sheet B can be covered completely with the first and second films F1 and F2 and hence, it is also possible to reliably prevent the generation of a dust from a cut face of the outer periphery of the base paper sheet B. In addition, the direct bonding of the films F1 and F2 to each other can be conducted relatively easily and reliably, leading to the simplification of the bonding process.

Further, the flat back-side air layer Ad is formed between the second film F2 and the back of the humidity-determining plate P, so that at least the regions of the back corresponding to the humidity-determining faces M1 to M4 face to the flat back-side air layer Ad, and the plurality of small holes H' are formed at the distances from one another in the second film F2 to permit the direct communication of the back-side air layer Ad with the atmosphere. Therefore, when the humidity indicator I has been taken in the atmosphere out of the packaging bag DP or the like, the moisture in the atmosphere is transmitted from the back side of the base paper sheet B through the back-side air layer Ad and the inside of the base paper sheet B even to the surface-side air layer Au. Accordingly, it is possible to more enhance the sensitivity of portions of the humidity-determining faces M1 to M4 on the side of the surface to the change in humidity.

Although the embodiment of the present invention has been described in detail, it will be understood that various modifications in design may be made without departing from the subject matter of the present invention.

For example, in the above-described embodiment, the four quadrilateral humidity-determining faces M1 to M4 which are discolored when the humidity in the atmosphere is increased to be equal to or more than four-stage limit humidity values (5%, 10%, 20% and 30%) are shown as being arranged longitudinally and transversely on the surface of the base paper sheet B, but according to the present invention, the limit humidity values, the number of pieces, the arrangement, the shape and the like for the humidity-determining faces may be selected as desired and are not limited to those in the above-described embodiment.

In addition, in the above-described embodiment, the surface-side air layer Au is formed into the planar shape including all of the humidity-determining faces M1 to M4 and as the common air layer to which all of the humidity-determining faces M1 to M4 face, but according to the present invention, surface-side air layers Au may be formed on every individual humidity-determining faces or on every group of several humidity-determining faces. This point likewise applies to the backs-side air layer Ad.

Further, in the above-described embodiment, the air layers Au and Ad are shown as being formed on the surface and back of the humidity-determining plate P, respectively, but according to the present invention (excluding Claim 4), the back-side air layer Ad as the second air layer may be omitted.

Yet further, in the above-described embodiment, the first and second films F1 and F2 are shown as being formed at the size larger than the base paper sheet B, so that the outer peripheral edges F1a and F2a of the films F1 and F2 are bonded directly to each other (in the thermo-compression manner), but according to the present invention (excluding Claim 2), the first and second films F1 and F2 may be formed into the same shape as the base paper sheet B and bonded to the surface and back of the base paper sheet B in the thermo-compression manner, or bonded directly to the surface and back of the base paper sheet B through an adhesive or the like.

The invention claimed is:

1. A humidity indicator, comprising at least one humidity-determining face which is provided on a surface of a humidity-determining plate comprising cobalt chloride held in a base paper sheet, so that the cobalt chloride is exposed to the humidity-determining face, whereby humidity is determined by the discoloration of the cobalt chloride on the humidity-determining face, characterized in that said humidity indicator further includes a first film covering the surface of said humidity-determining plate, and a second film covering the back of said humidity-determining plate;

a flat air layer is formed at least between the first film and the surface of the humidity-determining plate, so that the entire surface of said humidity-determining face faces to said air layer;

a plurality of small holes are formed at distances from one another in said first film to permit the direct communication of said air layer with the atmosphere;

said first and second films are formed to protrude from an outer peripheral edge of said humidity-determining plate and bonded at outer peripheral edge portions thereof directly to each other; and said first and second films are bonded in a compression manner to a portion of said humidity-determining plate surrounding a region corresponding to said air layer.

2. The humidity indicator according to claim 1, wherein a plurality of said humidity-determining faces are arranged at distances on the surface of said humidity-determining plate in correspondence to a plurality of different humidity levels, respectively; and said air layer is formed commonly to a plurality of said humidity-determining faces.

3. The humidity indicator according to claim 1 or 2, wherein said base paper sheet is a filter paper having a hygroscopicity;

a flat second air layer is formed between said second film and the back of said humidity-determining plate, so that at least a region or regions of said back corresponding to said humidity-determining face or faces face to the second air layer; and a plurality of small holes are formed at distances from one another in said second film to permit the direct communication of said second air layer with the atmosphere.

4. The humidity indicator according to claim 1 or 2, wherein that each of said films has been subjected to an antistatic treatment.

5. The humidity indicator of claim 1, wherein said humidity indicator is transported with an electronic part in a packaged state.

6. A humidity indicator, comprising at least one humidity-determining face which is provided on a surface of a humidity-determining plate which is made of a paper and formed into a card-shape, whereby humidity is determined by the discoloration of the humidity-determining face characterized in that said humidity indicator further includes a first film covering the surface of said humidity-determining plate and forming the surface of said humidity indicator, and a second film covering the back of said humidity-determining plate and forming the back of said humidity indicator;

a flat air layer is formed at least between the first film and the surface of the humidity-determining plate, so that the entire surface of said humidity-determining face faces to said air layer;

a plurality of small holes are formed at distances from one another in said first film to permit the direct communication of said air layer with the atmosphere;

said first and second films are formed to protrude from an outer peripheral edge of said humidity-determining plate and bonded at outer peripheral edge portions thereof directly to each other; and said first and second films are bonded in a compression manner to a portion of said humidity-determining plate surrounding a region corresponding to said air layer.

7. The humidity indicator according to claim 6, wherein a plurality of said humidity-determining faces are arranged at distances on the surface of said humidity-determining plate in correspondence to a plurality of different humidity levels, respectively; and said air layer is formed commonly to a plurality of said humidity-determining faces.

8. The humidity indicator according to claim 6 or 7, wherein said base paper sheet is a filter paper having a hygroscopicity;

a flat second air layer is formed between said second film and the back of said humidity-determining plate, so that at least a region or regions of said back corresponding to said humidity-determining face or faces face to the second air layer; and a plurality of small holes are formed at distances from one another in said second film to permit the direct communication of said second air layer with the atmosphere.

9. The humidity indicator according to claim 6 or 7, wherein that each of said films has been subjected to an antistatic treatment.

10. The humidity indicator of claim 6, wherein said humidity indicator is transported with an electronic part in a packaged state.

* * * * *